US008269032B1

(12) United States Patent
Fleming et al.

(10) Patent No.: US 8,269,032 B1
(45) Date of Patent: Sep. 18, 2012

(54) COMPOSITION, SYNTHESIS, AND USE OF ISONITRILES

(75) Inventors: Fraser Ferguson Fleming, Sewickley, PA (US); Bhaskar Reddy Pitta, Pittsburgh, PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 10 days.

(21) Appl. No.: 13/080,179

(22) Filed: Apr. 5, 2011

(51) Int. Cl.
*C07C 249/00* (2006.01)

(52) U.S. Cl. ........................................................ 558/302

(58) Field of Classification Search ........................ None
See application file for complete search history.

(56) References Cited

FOREIGN PATENT DOCUMENTS

| | | | |
|---|---|---|---|
| DE | 128531 | * | 11/1977 |
| JP | 2002-134168 | * | 5/2002 |
| WO | WO 02/20487 | * | 3/2002 |

OTHER PUBLICATIONS

Trost, Barry M., "Methyl 2-Pyridinesulfinate. A Convenient Reagent for Sulfinylation-Dehydrosulfinylation", Journal of Organic Chemstry, 58, 1579-1581, 1993.*

Van Leusen, Albert M., "The Effect of Sulfur-Substituents on the Chemistry of Alkyl Isocyanides",Studies in Organic Chemistry/ Amsterdam, 28 (Perspectives in the Organic Chemistry of Sulfur), 119-144, 1987.*

Machine Translation of JP 06-247944, 1994. (Parts 1 & 2).*

Tandon, Vishnu K. et al., "p-Toluenesulfonylmethyl Isocyanide: A Versatile Synthon in Organic Chemistry", Sulfur Reports, 24(3), 307-385, 2003.*

Casey Mike et al., "Synthetically Useful Desulfurisation Reactions of Heteroaryl Sulfoxide Conjugate Adducts", Synlett, 12, 1725-1728, 2000.*

Cheng, Wei-Chieh et al., "Vinyl Sulfones in Solid-Phase Synthesis: Preparation of 4,5,6,7-Tetrahydroisoindole Derivatives", Journal of Organic Chemistry, 66, 5528-5533, 2001.*

* cited by examiner

*Primary Examiner* — Fiona T Powers

(74) *Attorney, Agent, or Firm* — Eckert Seamans Cherin & Mellott, LLC; Carol A. Marmo

(57) ABSTRACT

The present invention relates to isonitrile compounds, methods of synthesis, and uses in a variety of fields. In one aspect, the present invention includes sulfinyl methyl isonitriles and methods for their preparation. In another aspect, the present invention includes the use of sulfinyl methyl isonitriles to prepare various other isonitrile compounds and derivatives thereof. In yet another aspect, the present invention includes a relatively simple and routine synthesis of sulfinyl methyl isonitrile compounds, other isonitrile compounds and derivatives thereof.

23 Claims, 4 Drawing Sheets

3a 3b 4

1 2a 2b 17 11 12 15 13 49 16

8 8a 9

9 10

74

9

75

76

77

78

79

COMPOSITION, SYNTHESIS, AND USE OF ISONITRILES

FIELD OF THE INVENTION

The present invention relates to isonitriles and their synthesis. Further, the present invention relates to the uses of isonitriles. In particular, the present invention relates to preparing sulfinyl methyl isonitriles and their use as building blocks to produce various other isonitriles and their use in multicomponent reactions.

BACKGROUND

Isonitrile compounds and derivatives thereof are known in the art and can be used in various applications, including the fields of medicine and pharmaceuticals. For example, bioactive isonitrile-containing metabolites are being increasingly isolated and are considered among the best small-molecule leads for addressing the 300-500 million infections and 1-3 million deaths caused annually by malaria. The spread of resistant strains and the rise in global temperatures make this one of the highest priorities of the World Health Organization for the third world and North America.

Various methods for synthesizing isonitrile compounds are also known in the art. For example, it is known that isonitriles can be synthesized by the reaction of primary amines with dichlorocarbene or by dehydration of a formamide with phosphorus oxychloride. The Hofmann synthesis is a chemical test for primary amines based on their reaction with potassium hydroxide and chloroform as dichlorocarbene precursors to isonitriles. Another route to producing isonitriles is by reaction of organolithium compounds with oxazoles and benzoxazoles. A further synthetic route toward isonitriles includes condensation of an amine with formic acid to yield a formamide, and subsequent dehydration of this formamide. Phosgene can be used in combination with the formamide to yield isonitriles.

Isonitriles are used as reactants in multi-component Ugi and Passerini condensations, heterocycle synthesis, in radical and Pauson-Khand reactions and as ligands and in medical imaging.

There are disadvantages associated with the known methods of synthesizing isonitriles. The deprotonation-alkylation syntheses are limited to special substrates and conjugate additions with alkylisonitriles are rare, extremely challenging, and require additional activation through further conjugation. Further, alkyneisonitriles are virtually unknown except as components of interstellar gases and their reactivity remains relatively unexplored. The dearth of isonitrile-based methodology may be preventing direct, rapid access to bioactive isonitrile-containing carbocycles. Recourse to multi-step sequences is often required. For example, the synthesis of an anti-fouling isonitrile may require as many as ten steps to convert a ketone into an isonitrile.

The commercial availability of isonitriles is limited and those that are commercially available can be expensive.

Thus, there is a need in the art to develop new connectivity methods, access isonitriles having new structural diversity, reveal fundamental reactivity patterns in alkylations and conjugate additions, and establish the essential principles for performing transition metal catalysis with isonitriles. Furthermore, it would be advantageous if the isonitriles can be produced in a minimum number of steps, are cost effective to produce and result in high yields.

SUMMARY OF THE INVENTION

In one aspect, the present invention provides a sulfinyl methyl isonitrile compound having a general structure represented by formula

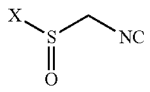

wherein X is selected from the group consisting of hydrogen, substituted and un-substituted, aliphatic and non-aliphatic, hydrocarbon, branched and un-branched alkyl, alkenyl, alkynyl, cycloalkyl having one or more rings, aryl including benzyl, phenyl, thienyl, indoyl, heteroaryl, combinations thereof and derivatives thereof.

In another aspect, the present invention provides a method of preparing a sulfinyl methyl isonitrile compound having the above formula. The method includes treating an isocyanomethane with an organometallic reagent to form a first mixture, combining the first mixture with an alkyl aryl sulfinate to form a second mixture, and extracting the sulfinyl methyl isonitrile.

In still another aspect, the present invention provides a method of preparing a substituted isonitrile. The method includes treating a sulfinyl methyl isonitrile having a sulfinyl group, the sulfinyl group including a cyclic or an acyclic compound, with an organometallic reagent to remove and replace the sulfinyl group with a metal to form a metalated isonitrile, and treating the metalated isonitrile to remove and replace the metal with a group R to form the substituted isonitrile, the group selected from the group consisting of carbon-containing groups, such as, but not limited to, alkyl, alkenyl, alkynyl, carbonyl, olefin, and combinations thereof, sulfur-containing groups, oxygen-containing groups, and combinations thereof.

In yet another aspect, the present invention provides a method of preparing an unsaturated isonitrile. The method including treating an isonitrile with an organometallic reagent and an alkyl aryl sulfinate to form a sulfinyl methyl isonitrile having a sulfinyl group; and treating the sulfinyl methyl isonitrile to remove a sulfoxide group to form the unsaturated isonitrile.

BRIEF DESCRIPTION OF THE DRAWINGS

The various embodiments of the present disclosure may be better understood when read with reference to the following figures.

DETAILED DESCRIPTION OF THE INVENTION

Figure 1:
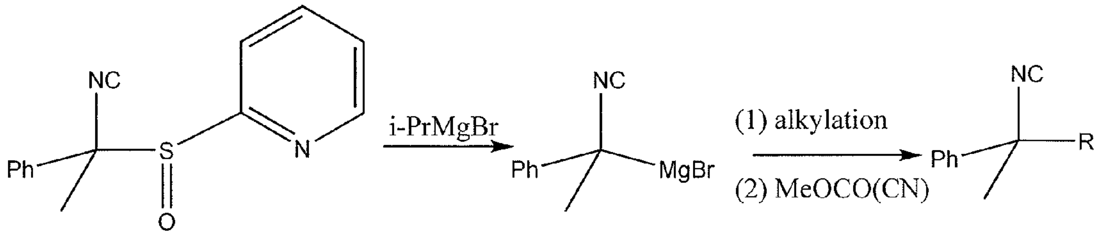
FIG. 1 illustrates a sulfinyl exchange reaction scheme in accordance with an embodiment of the present invention.

The present invention relates to isonitrile compounds, their synthesis, and uses thereof. In one aspect, the present invention includes sulfinyl methyl isonitriles and their synthesis. In the art, the term "sulfinyl methyl isonitrile" may be identified using various other names, such as "sulfoxide methyl isonitrile" and "isonitrile methyl sulfoxide." Herein and in the claims, the term "sulfinyl methyl isonitrile" will be used and is to be understood to encompass "sulfoxide methyl isonitrile," "isonitrile methyl sulfoxide," and the like. In another aspect, the present invention includes the use of sulfinyl methyl isonitriles as building blocks or precursors to prepare various other isonitrile compounds and derivatives thereof. In yet another aspect, the present invention includes a relatively simple and routine synthesis of sulfinyl methyl isonitrile compounds, other isonitrile compounds (e.g., substituted isonitriles) and derivatives thereof.

Other than the operating examples, or where otherwise indicated, all numbers expressing quantities of ingredients, processing conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, may contain certain errors, such as, for example, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

The present disclosure describes several different features and aspects of the invention with reference to various exemplary non-limiting embodiments. It is understood, however, that the invention embraces numerous alternative embodiments, which may be accomplished by combining any of the different features, aspects, and embodiments described herein in any combination that one of ordinary skill in the art would find useful.

The present invention relates to the development of a new sulfinyl methyl isonitrile having a general structure represented by formula I.

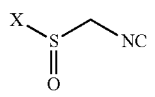

(I)

In formula I, the X group includes hydrogen, substituted and un-substituted, aliphatic and non-aliphatic, hydrocarbon, branched and un-branched alkyl, such as $C_1$-$C_6$ alkyl, alkenyl, alkynyl, cycloalkyl having one or more rings, aryl including benzyl, phenyl, thienyl, indoyl, heteroaryl, combinations thereof and derivatives thereof.

The sulfinyl methyl isonitrile, as represented by the general structure of formula I, can be readily synthesized using organic chemistry techniques. In accordance with an embodiment of the present invention, the synthetic approach can start with an isocyanomethane treated with an organometallic reagent. The organometallic reagent can be in an organic solvent. The organic solvent can be selected from those known in the art including hydrocarbon, ether, and mixtures thereof. Non-limiting examples include cyclohexane, tetrahydrofuran, a mixture of hexanes, and mixtures thereof. In one embodiment, the organometallic reagent is in cyclohexane. Further, the isocyanomethane can be in an organic solvent including those described above. In one embodiment, the isocyanomethane is in tetrahydrofuran. The organometallic reagent can be selected from a variety of such materials known in the art. Non-limiting examples can include organolithium, organozinc, organomagnesium, and mixtures thereof. In one embodiment, the organometallic reagent is n-butyl lithium.

The mixture of organometallic reagent, isocyanomethane, and solvent is combined with an alkyl aryl sulfinate. The alkyl aryl sulfinate can be selected from those known in the art. In one embodiment, the alkyl aryl sulfinate is methylpyridine-2-sulfinate. The alkyl aryl sulfinate can be in an organic solvent. The organic solvent can be selected from those described above. In one embodiment, the organic solvent is tetrahydrofuran.

The mixture of organometallic reagent, isocyanomethane, solvent, and alkyl aryl sulfinate is allowed to set for a period of time. For example, the mixture can set for approximately thirty minutes. A quenching solution is then added. The quenching solution can be selected from those known in the art. Non-limiting examples can include aqueous ammonium chloride, brine, water, aqueous sodium bicarbonate, and mixtures thereof. In one embodiment, the quenching solution is aqueous ammonium chloride.

The sulfinyl methyl isonitrile compound is then extracted from the mixture using conventional extraction techniques known in the art. In one embodiment, an organic compound can be added to the mixture to extract the product. The organic compound can be selected from those known in the art and can include, but is not limited to, dichloromethane, ethyl acetate, ether, and mixtures thereof. In one embodiment, the organic compound is dichloromethane.

The extracted product is then dried in accordance with conventional drying techniques known in the art. The dried, extracted product is then purified using conventional purifying techniques known in the art. In one embodiment, the purification is conducted by radial chromatography.

The yield of the product can vary and, for example, the yield can be 65% or greater.

In one embodiment of the present invention, the product is 2-((isocyanomethyl)sulfinyl)pyridine having a structure represented by formula II.

(II)

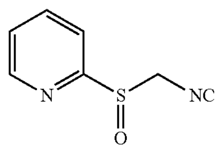

It is preferable to prepare the sulfinyl methyl isonitriles having a structure represented by formulas I and II, and subsequent substituted isonitriles, using relatively simple and routine synthetic approaches. Further, it is desirable for the product to be synthesized in a minimal number of steps. In accordance with the present invention the sulfinyl methyl isonitriles and various other isonitriles, and derivatives thereof, formed using the sulfinyl methyl isonitriles as a building block or precursor, can be prepared using relatively simple and routine synthesis approaches and a minimal number of steps.

In one embodiment, metalated isonitriles are prepared using a sulfinyl methyl isonitrile in accordance with the present invention as a starting material, e.g., building block. The sulfinyl methyl isonitrile undergoes a sulfinyl-metal exchange in mild conditions. The sulfinyl methyl isonitrile is treated with an organometallic reagent. The organometallic reagent can be selected from those materials described above. The sulfinyl group is removed. The sufinyl group can include a cyclic or an acyclic compound. The sulfinyl group is exchanged and replaced with a metal or metal-containing group to form a metalated isonitrile. The metal can be selected from a variety of metals known in the art, including transition metals. Non-limiting examples include magnesium, lithium, and zinc.

A certain specific example is discussed in detail in FIG. 1. As illustrated in FIG. 1, the synthetic approach begins with a sulfinyl methyl isonitrile 3a treated with isopropyl magnesium bromide. The sulfinyl group is removed and replaced with the metal group MgBr to form a magnesiated isonitrile 3b. In one embodiment, the magnesiated (e.g., metalated) isonitrile 3b undergoes a subsequent treatment, e.g., alkylation, to remove and replace the MgBr, e.g., metal group, with another group, R, e.g., alkyl, to form a substituted isonitrile. In another embodiment, in accordance with FIG. 1, the magnesiated isonitrile 3b is treated with cyanoformate (MeOCO(CN)) such that the MgBr of the magnesiated isonitrile 3b is removed and replaced with an ether, e.g., R is ether. In FIG. 1, Ph is phenyl, and R includes substituted and un-substituted, aliphatic and non-aliphatic, hydrocarbons, branched and unbranched alkyl, such as $C_1$-$C_6$ alkyl, hydroxy $C_1$-$C_6$ alkyl, amino $C_1$-$C_6$ alkyl, thio $C_1$-$C_6$ alkyl, carboxy $C_1$-$C_6$ alkyl, alkenyl, alkynyl, cycloalkyl having one or more rings, aryl including benzyl, phenyl, thienyl, indoyl, heteroaryl, carbonyl, olefin, ether, sulfur-containing groups, oxygen-containing groups, and combinations thereof.

The sulfinyl methyl isonitriles having a structure represented by formulas I and II can be used to synthesize various substituted isonitriles and isonitrile derivatives. In one embodiment, the sulfinyl methyl isonitrile is used as a building block in alkylation reactions. Without intending to be bound by any particular theory, it is believed that condensing lithiomethylisonitrile with the corresponding sulfinate should render the sulfinyl methyl isonitrile (e.g., formulas I and II) as a potentially odorless isonitrile trianion equivalent. The synthetic approach may start with alkylating the sulfinyl methyl isonitrile with dibromo- and diido-alkanes to form an intermediate. Subsequently, alkylating the intermediate with bifunctional electrophiles, such as methyl bromopentanoate and 1,4-dibromopentane, to form another intermediate. It is contemplated to conduct sequential alkylations with two different electrophiles.

Figure 2:
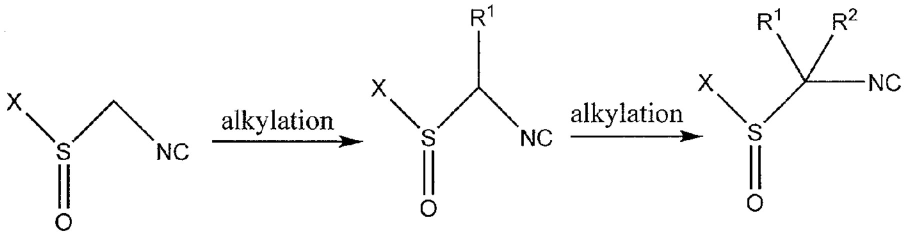
FIG. 2 illustrates an alkylation synthesis of sulfinyl methyl isonitriles in accordance with an embodiment of the present invention.

A specific example is discussed in detail in FIG. 2. As illustrated in FIG. 2, the sulfinyl methyl isonitrile 1 is alkylated to form the intermediate 2a. The intermediate 2a is alkylated to form the intermediate 2b. In FIG. 2, the X group is defined as recited above for formula I. Each of $R^1$ and $R^2$ is alkyl or cycloalkyl. $R^1$ and $R^2$ may be the same or different. The intermediates 2a and 2b may be used in subsequent reactions to produce various substituted isonitriles and isonitrile derivatives. For example, the sulfinyl methyl isonitrile 1 and, the intermediates 2a and 2b, may be subjected to an elimination reaction to form an alkene isonitrile or subjected to a metal (e.g., magnesium) exchange to form a metalated (e.g., magnesiated) isonitrile. These reaction schemes are later herein described in more detail.

Further, condensing the sulfinyl methyl isonitrile with aldehyde is expected to provide alkenesulfonyl isonitriles having the general structure represented by formula III.

(III)

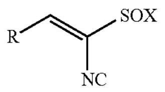

wherein X is defined as in formula I and R is alkyl or cycloalkyl.

For condensations with aliphatic aldehydes, the compound of formula III can be subjected to mild deconjugation-rearrangement to form a compound having the general structure represented by formula IV.

(IV)

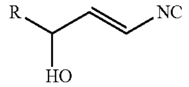

wherein R is defined as in formula III.

Figure 3:
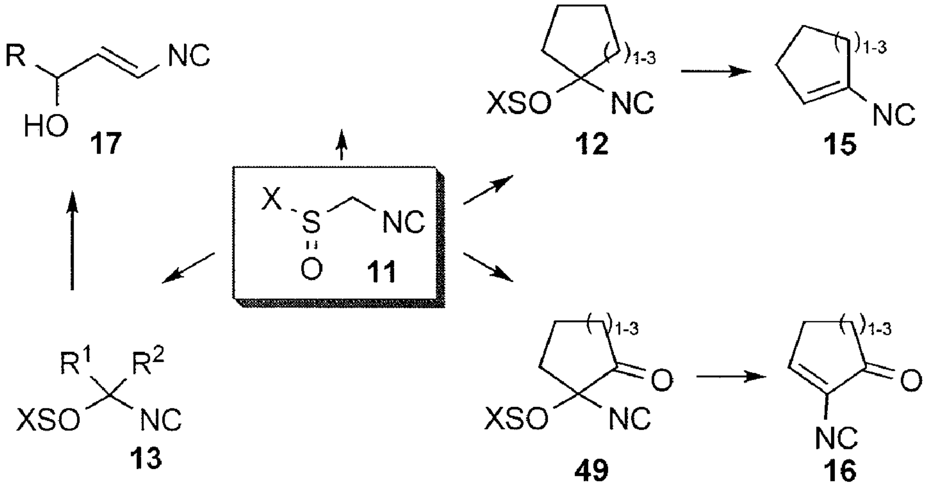
FIG. 3 illustrates sulfinyl isonitrile syntheses via alkylations in accordance with an embodiment of the present invention.

Sulfinyl isonitriles may be readily desulfinylated. This process may depend on the particular aromatic selected. A specific example is discussed in detail in FIG. 3 including the starting sulfinyl methyl isonitrile 11. As illustrated in FIG. 3, it is contemplated that the sulfinyl alkeneisonitriles 12, 13 and 49 may be desulfinylated and should generate the corresponding alkeneisonitriles 15, 17, and 16, respectively. In FIG. 3, X is as defined for formula I and, R, $R^1$ and $R^2$ each independently can be alkyl or cycloalkyl. R, R1 and R2 can be the same or different. It is further contemplated that these alkenenitriles 15, 17, and 16 can be used in conjugate addition and Diels-Alder reactions, and in multi-component reactions.

In the present invention, unsaturated isonitriles, such as, but not limited to alkene isonitriles, are synthesized in accordance with the following embodiment. A sulfinyl methyl isonitrile compound undergoes sulfoxide elimination to produce the unsaturated isonitrile. An isonitrile is treated with an organometallic reagent and sulfinylated to produce a sulfinyl methyl isonitrile compound. The organometallic reagent can be selected from those described above. In one embodiment, the organometallic reagent is n-butyllithium. The sulfinylation can be performed with an alkyl aryl sulfinate. In one embodiment, the alkyl aryl sulfinate is methyl pyridine-2-sulfinate. The isonitrile starting material can be selected from a variety of isonitriles available in the art. In one embodiment, the isonitrile is a phenyl isonitrile.

Figure 4:
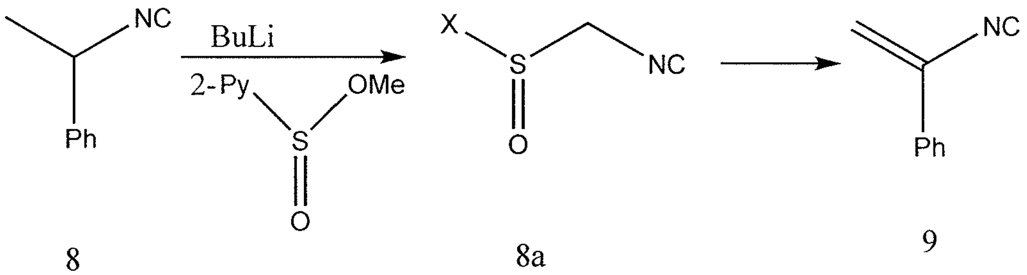
FIG. 4 illustrates an alkeneisonitrile synthesis in accordance with an embodiment of the present invention.

A specific example is discussed in detail in FIG. 4. As illustrated in FIG. 4, the synthetic approach begins with a phenyl isonitrile 8 treated with n-butyl lithium and sulfinylated with methylpyridine-2-sulfinate to produce a sulfinyl methyl isonitrile 8a. The sulfinyl methyl isonitrile 8a undergoes sulfoxide elimination to produce the unsaturated isonitrile, α-phenylvinylisonitrile 9 (e.g., alkene isonitrile). In FIG. 4, X is as defined in formula I and Ph is phenyl.

Without intending to be bound by any particular theory, it is believed that a nucleophile can be added, e.g., by conjugate addition to a vinylisonitrile, to form a substituted isonitrile. The addition of the nucleophile can be performed in the presence of a catalyst selected from those known in the art, such as, but not limited to, a palladium catalyst. In one embodiment, the catalyst is a palladium pincer catalyst.

Figure 5:
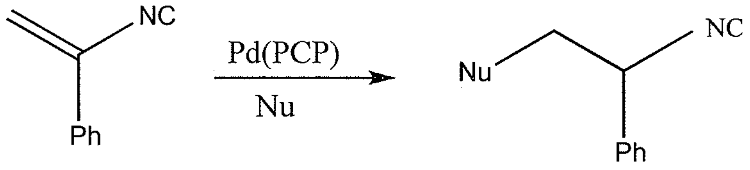
FIG. 5 illustrates a conjugate addition synthesis to a vinylisonitrile in accordance with an embodiment of the present invention.

A specific example is discussed in detail in FIG. 5. As illustrated in FIG. 5, a nucleophile Nu is added to α-phenylvinylisonitrile 9 in the presence of Pd(PCP) as catalyst to produce a nucleophile-substituted isonitrile 10. Further, in FIG. 5, Ph represents phenyl.

In another embodiment, the sulfoxide elimination of an isonitrile, as shown in FIG. 5, can be used to prepare an alkyneisonitrile.

The alkyl aryl sulfinate used for the sulfinylation step in the sulfoxide elimination reaction scheme can also include 4-$CF_3$PhSO(OMe). Without intending to be bound by any particular theory, it is believed that the elimination of sulfoxide may be accelerated when the sulfoxide includes an electron deficient aromatic substituent thereon.

Further, without intending to be bound by any particular theory, it is believed the unsaturated isonitrile α-phenylvinylisonitrile 9 (as shown in FIGS. 4 and 5) is particularly suitable for developing conjugate additions because phenyl substitution facilitates the nucleophilic attack.

Moreover, a catalyst for the reaction scheme (as shown in FIG. 5) can include a combination of a low valent metal with a sterically-demanding ligand. Without intending to be bound by any particular theory, it is believed that this combination is favorable to turnover without irreversible binding to the isonitrile. Of the catalyzed reactions with isonitriles, insertion reactions can predominate because ligation to a metal center binds the electrophilic isonitrile and facilitates internal and external nucleophilic attack. The low valent metal can be selected from those known in the art and preferably includes those that have demonstrated isonitrile-ligand exchange. Non-limiting examples can include palladium pincer complexes. In one embodiment, the low valent metal is palladium. The sterically-demanding ligand can be selected from those known in the art. Non-limiting examples include alkyl PCP ligands, phosphoramide PCP and PNP ligands, PCP N-heterocyclic carbene ligands, and mixtures thereof. The use of electron-rich ligands can increase the electron density on the metal and decrease an affinity toward the isonitrile.

In one embodiment, the low valent metal and ligand combination includes a palladium pincer complex. The palladium pincer complex catalyzes aldol-type condensations of methyl isocyanoacetate with aldehydes and imines. In addition, the modular construction of the pincer ligands can provide for tuning of the steric demand and the electron density on the palladium center to favor reversible isonitrile binding.

The unsaturated isonitrile, e.g., alkene isonitrile, such as α-phenylvinylisonitrile 9 (as shown in FIGS. 4 and 5), can be used with ethanol and aniline nucleophiles in a conjugate addition reaction to form a substituted isonitrile. The ethanol can be used in excess and/or at elevated temperatures to form β-alkoxyisonitriles. The β-alkoxyisonitriles can be used as ligands in myocardial perfusion and as hyperparathyroidism tracers in tumor imaging.

Figure 6:
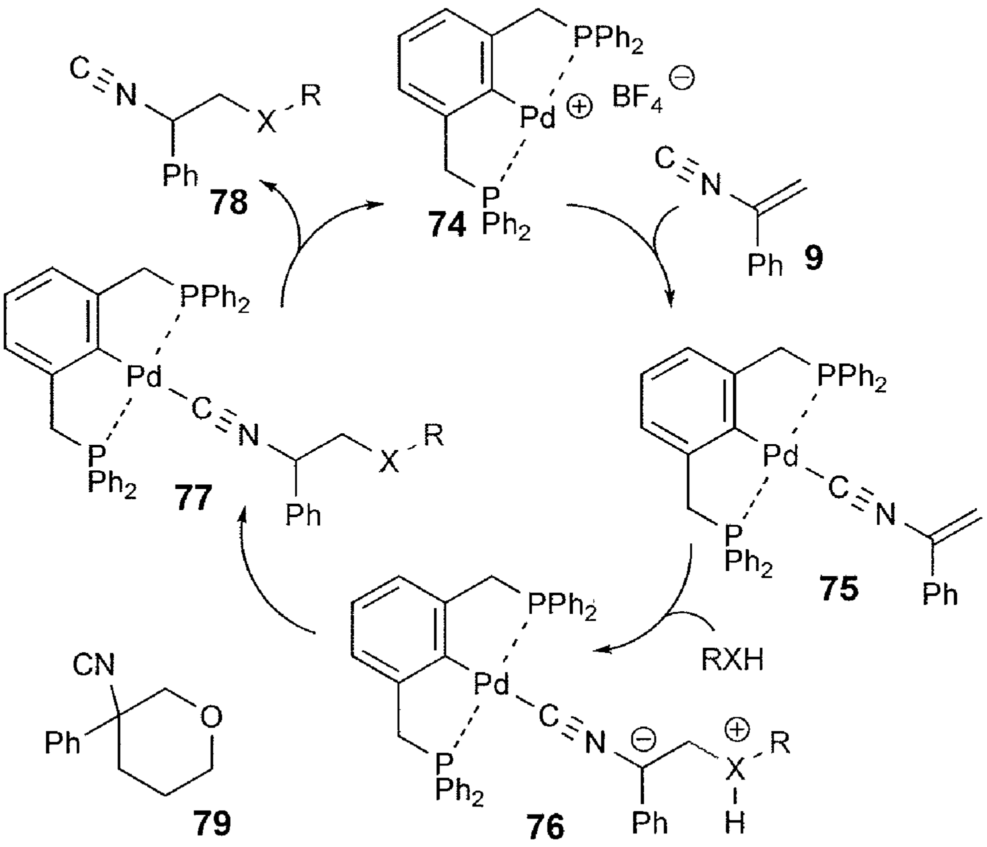
FIG. 6 illustrates pincer catalyzed isonitrile conjugate addition in accordance with an embodiment of the present invention.

A specific example is discussed in detail in FIG. 6. As illustrated in FIG. 6, the group X-R can include oxygen-containing compounds, such as, hydroxyl-containing compounds including, but not limited to, hydroxy $C_1$-$C_6$ alkyl (e.g., alcohol), nitrogen-containing compounds, such as amines including, but not limited to, amino $C_1$-$C_6$ alkyl, carbon-containing compounds, such as carbon nucleophiles including but not limited to alkyl metal halides, and Ph is phenyl. The complexation of the α-phenylvinylisonitrile 9 to the pincer complex 74 can form the active complex 75 for external attack by ethanol. Subsequent proton transfer between the zwitterion 76 and excess ethanol can be directly analogous to pincer catalyzed aldol-type condensations. Forming the neutral complex 77 may facilitate the decomplexation because the α-phenylvinylisonitrile 9 has a reduced steric demand relative to the neutral complex 77 and is an improved π-acceptor to form the resulting isonitrile 78.

In one embodiment, the conjugate addition can be performed with water or salicylaldehyde. Without intending to be bound by any particular theory, it is believed that installing a free hydroxyl may facilitate cyclization to the metalated oxazaline. Analogous cyclizations are used extensively to form metal carbenes. Further, it is believed that subsequent protonation should release the oxazoline.

In another embodiment, conjugate addition can be performed with a combination of 3-chloropropanol and potassium t-butoxide (t-BuOK). Without intending to be bound by any particular theory, it is believed that Michael addition should generate an intermediate anion that triggers ring closure to form pyran 79. Installing the sterically demanding quaternary center should create significant steric demand around the metal-ligand framework facilitating the release of the isonitrile.

The sulfinyl methyl isonitriles and the substituted isonitriles produced therefrom, in accordance with the present invention, have various uses and applications. These compounds are particularly suitable for use in multi-component reactions and, in the fields of medicine and pharmaceuticals.

EXAMPLE

Two moles of a cyclohexane solution of BuLi (1.218 mmol, 1 equiv.) was added to 4 mL of a tetrahydrofuran solution of isocyanomethane (50 mg, 1.218 mmol, 10 equiv.) at a temperature of −78° C. After ten minutes, 0.5 mL of a THF solution of methylpyridine-2-sulfinate (210 mg, 1.34 mmol, 11 equiv.) was added at once. After thirty minutes, 5 mL of saturated, aqueous $NH_4Cl$ was added. A crude product was extracted with $CH_2$ $Cl_2$ (2×15 mL), dried ($NaSO_4$), and concentrated. The crude product was purified by radial chromatography (1 mm alumina plate, 30:70 ethylacetate/hexanes) to produce 131 mg (65% yield) of 2-((isocyanomethyl) sulfinyl)pyridine as a white solid having M.P. 91-93° C.; IR (film) 542, 776, 960, 992, 1038, 1053, 1427, 1452, 1578, 2139, 2923, 2997 $cm^{-1}$; NMR: δ 4.73 (ABq, Δv=83.3 Hz, J=14.3 Hz, 2H), 7.49-7.52 (m, 1H), 8.04-8.12 (m, 2H), 8.67-8.68 (m, 1H); $^{13}C$ NMR: δ 60.33, 125.65, 125.82, 138.56, 150.02, 160.58, 165.10.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of preparing a sulfinyl methyl isonitrile of the formula I

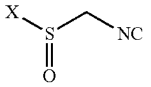

(I)

wherein X is selected from the group consisting of hydrogen, substituted and unsubstituted, aliphatic and non-aliphatic, hydrocarbon, branched and un-branched alkyl, alkenyl, alkynyl, cycloalkyl having one or more rings, aryl, heteroaryl, and combinations thereof, comprising:

treating an isocyanomethane with an organometallic reagent to form a treated isocyanomethane;

combining the treated isocyanomethane with an alkyl aryl sulfinate to form a mixture, the mixture comprising the sulfinyl methyl isonitrile of the formula I; and extracting the sulfinyl methyl isonitrile of the formula I from the mixture.

2. The method of claim 1 wherein the isocyanomethane is in organic solvent.

3. The method of claim 2 wherein the organic solvent is tetrahydrofuran.

4. The method of claim 1 wherein the organometallic reagent is selected from the group consisting of organolithium, organozinc, organomagnesium, and mixtures thereof.

5. The method of claim 4 wherein the organometallic reagent is n-butyllithium.

6. The method of claim 1 wherein the organometallic reagent is in organic solvent.

7. The method of claim 6 wherein the organic solvent is cyclohexane.

8. The method of claim 1 wherein the alkyl aryl sulfinate is in organic solvent.

9. The method of claim 8 wherein the organic solvent is tetrahydrofuran.

10. The method of claim 1 wherein the mixture further comprises a quenching component.

11. The method of claim 10 wherein the quenching component is aqueous ammonium chloride.

12. The method of claim 11 further comprising purifying following extracting to form a purified sulfinyl methyl isonitrile of the formula I.

13. The method of claim 12 wherein yield of the purified sulfinyl methyl isonitrile of the formula I is 65% or greater.

14. A method of preparing a substituted isonitrile, comprising:

treating a sulfinyl methyl isonitrile, the sulfinyl group comprising a cyclic or an acyclic group, with an organometallic reagent to remove and replace the sulfinyl group with a first group comprising metal to form a metalated isonitrile; and treating the metalated isonitrile to remove and replace the first group with a second group to form the substituted isonitrile, the second group selected from the group consisting of substituted and un-substituted, aliphatic and non-aliphatic, hydrocarbons, branched and un-branched alkyl, alkenyl, alkynyl, cycloalkyl having one or more rings, aryl, heteroaryl, carbonyl, olefin, ether, and combinations thereof.

15. The method of claim 14 wherein the second group is selected from the group consisting of $C_1$-$C_6$ alkyl, hydroxy $C_1$-$C_6$ alkyl, amino $C_1$-$C_6$ alkyl, thio $C_1$-$C_6$ alkyl, carboxy $C_1$-$C_6$ alkyl, benzyl, phenyl, thienyl, indoyl and combinations thereof.

16. A method of preparing an unsaturated isonitrile, comprising:

treating an isonitrile with an organometallic reagent and an alkyl aryl sulfinate to form a sulfinyl methyl isonitrile; and treating the sulfinyl methyl isonitrile to remove a sulfoxide group to form the unsaturated isonitrile.

17. The method of claim 16 wherein the unsaturated isonitrile is selected from the group consisting of alkene isonitriles and alkenyl isonitriles.

18. The method of claim 16 further comprising treating the unsaturated isonitrile with a catalyst and a nucleophile to undergo an addition reaction.

19. The method of claim 1 wherein the aryl is selected from the group consisting of benzyl, phenyl, thienyl, indoyl, and combinations thereof, and derivatives thereof.

20. The method of claim 1 wherein the alkyl is $C_1$ to $C_6$ alkyl.

21. The method of claim 1 wherein the sulfinyl methyl isonitrile of the formula I is 2-((isocyanomethyl)sulfinyl)pyridine of the formula II:

(II)

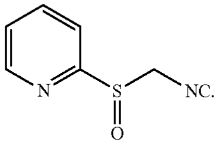

22. The method of claim 1 further comprising alkylating the sulfinyl methyl isonitrile of the formula I to form a first intermediate of the formula 2a and alkylating the first inter mediate to form a second intermediate of the formula 2b in accordance with the following reaction scheme:

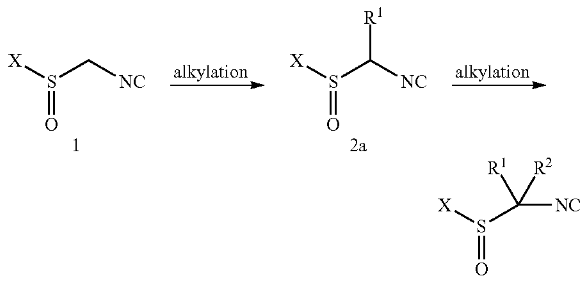

1 2a 2b wherein X is as defined in claim 1 for the formula 1, and each of $R^1$ and $R^2$ is the same or different, and each of $R^1$ and $R^2$ is selected from the group consisting of alkyl and cycloalkyl.

23. The method of claim 1 further comprising condensing the sulfinyl methyl isonitrile of the formula I with aldehyde to form alkenesulfonyl isonitrile of the formula III:

(III)

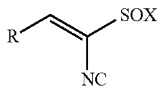

wherein X is as defined in claim 1 for the formula I, and

R is selected from the group consisting of alkyl and cycloalkyl.

* * * * *

UNITED STATES PATENT AND TRADEMARK OFFICE

CERTIFICATE OF CORRECTION

PATENT NO. : 8,269,032 B1
APPLICATION NO. : 13/080179
DATED : September 18, 2012
INVENTOR(S) : Fraser Ferguson Fleming et al.

It is certified that error appears in the above-identified patent and that said Letters Patent is hereby corrected as shown below:

Title page, first column, OTHER PUBLICATIONS, line 3, “Chemstry,” should read --Chemistry--.
Title page, second column, OTHER PUBLICATIONS, line 9, “Casey Mike et al.,” should read --Casey, Mike et al.,--.
Column 8, line 67, “NMR:” should read --$^{1}$H NMR:--.
Column 10, line 55, formula II, “NC.” should read --NC--.
Column 10, line 65, “inter” should read --inter- --.

Signed and Sealed this
Fifth Day of February, 2013

Teresa Stanek Rea
*Acting Director of the United States Patent and Trademark Office*